(12) United States Patent
Haecker

(10) Patent No.: US 12,220,516 B2
(45) Date of Patent: Feb. 11, 2025

(54) APPARATUS AND METHOD FOR TAKING A SAMPLE FROM A FLUID-CONDUCTING SYSTEM

(71) Applicant: FRESENIUS MEDICAL CARE DEUTSCHLAND GMBH, Bad Homburg (DE)

(72) Inventor: Juergen Haecker, Neu-Anspach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1455 days.

(21) Appl. No.: 16/070,173

(22) PCT Filed: Jan. 5, 2017

(86) PCT No.: PCT/EP2017/000007
§ 371 (c)(1),
(2) Date: Jul. 13, 2018

(87) PCT Pub. No.: WO2017/121631
PCT Pub. Date: Jul. 20, 2017

(65) Prior Publication Data
US 2019/0030234 A1 Jan. 31, 2019

(30) Foreign Application Priority Data
Jan. 15, 2016 (DE) ...................... 10 2016 000 370.7

(51) Int. Cl.
*A61M 1/36* (2006.01)
*A61B 5/145* (2006.01)
(Continued)

(52) U.S. Cl.
CPC .............. *A61M 1/367* (2013.01); *A61B 5/14* (2013.01); *A61M 1/1605* (2014.02);
(Continued)

(58) Field of Classification Search
CPC . B01L 3/0289; B01L 3/0296; A61M 2205/70; A61M 1/3609; A61M 1/1619;
(Continued)

(56) References Cited

U.S. PATENT DOCUMENTS 3,186,232 A * 6/1965 Buhl ........................ G01N 1/24
73/19.01
3,354,881 A * 11/1967 Bloch .................... A61M 5/326
604/199
(Continued)

FOREIGN PATENT DOCUMENTS

DE 102006062982 10/2014
WO WO 96/21393 7/1996
(Continued)

*Primary Examiner* — Ashley K Buran
*Assistant Examiner* — Helene Bor
(74) *Attorney, Agent, or Firm* — Jacobson Holman PLLC

(57) ABSTRACT

The present invention relates to an apparatus for sample taking from a fluid-conducting system, wherein the apparatus has at least one adapter which comprises at least one septum and at least one cannula displaceable relative to the septum, wherein the cannula is displaceable such that it penetrates the septum in a sample taking position and does not penetrate the septum in a flushing position; and wherein the adapter has at least one flushing region for a flushing medium which is arranged such that it is in fluid communication with the inner space of the cannula in the flushing position of the cannula; and wherein the apparatus has at least one receiving region having locking means for the fluid-conducting system by which the fluid-conducting system is fixable in a defined position relative to the adapter. The present invention furthermore relates to a blood treatment device and to a method for taking a sample from a fluid-conducting system.

17 Claims, 3 Drawing Sheets

Figure 1:
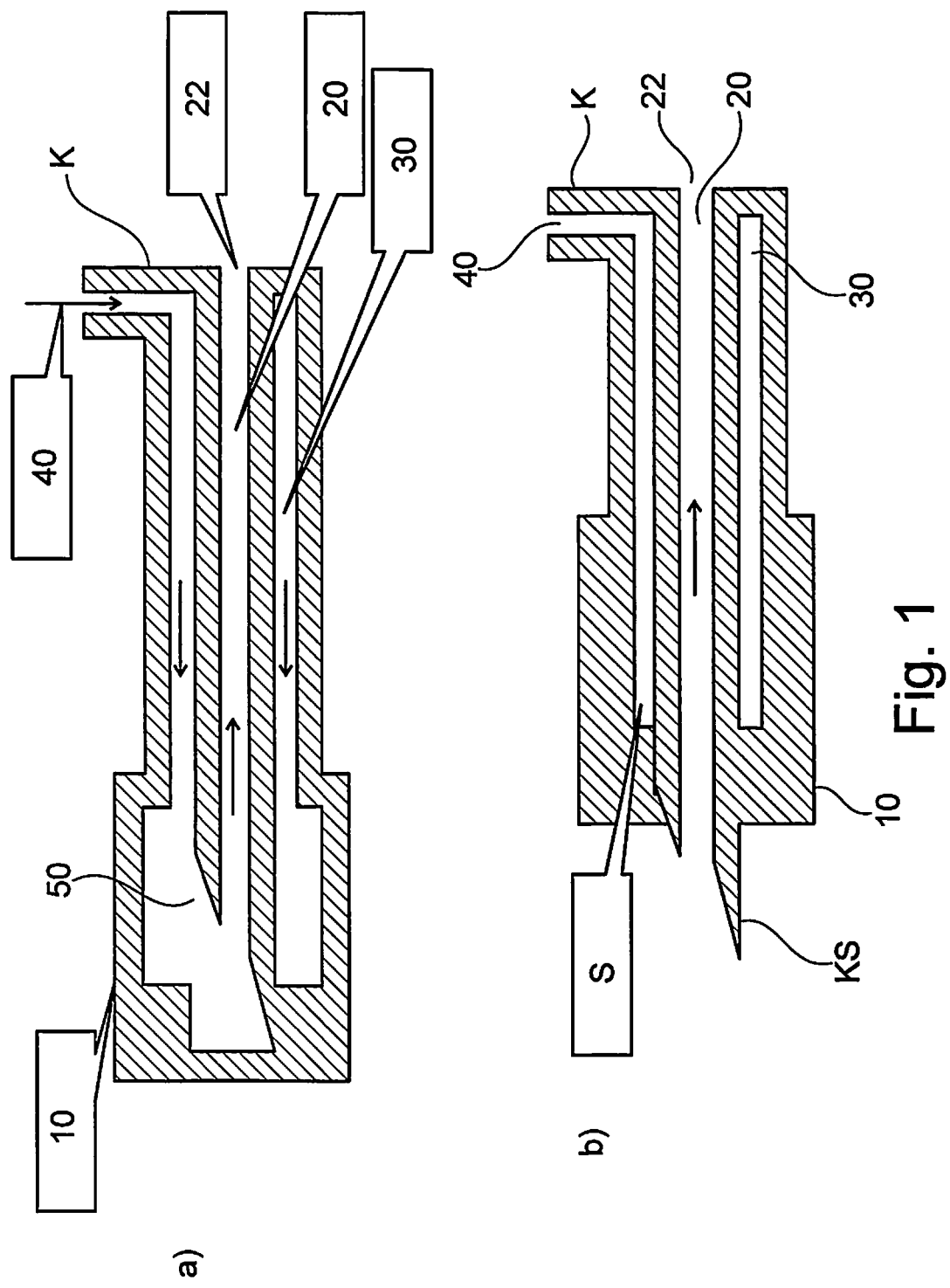

(51) Int. Cl.
*A61B 5/15* (2006.01)
*A61M 1/16* (2006.01)
*B01L 3/02* (2006.01)

(52) U.S. Cl.
CPC ........ *A61M 1/1619* (2014.02); *A61M 1/3609* (2014.02); *B01L 3/0296* (2013.01); *A61B 5/1405* (2013.01); *A61B 5/1433* (2013.01); *A61B 5/15* (2013.01); *A61B 5/150381* (2013.01); *A61B 5/150389* (2013.01); *A61M 2205/70* (2013.01); *B01L 3/0289* (2013.01)

(58) Field of Classification Search
CPC ........... A61M 1/1605; A61B 5/150389; A61B 5/150381; A61B 5/15; A61B 5/1433; A61B 5/1405; A61B 5/14
See application file for complete search history.

(56) References Cited

U.S. PATENT DOCUMENTS

| | | | | |
|---|---|---|---|---|
| 4,887,472 A | * | 12/1989 | Jansen | G01N 1/2035 73/863.86 |
| 4,920,970 A | * | 5/1990 | Wyatt | A61B 5/150992 604/201 |
| 5,055,203 A | * | 10/1991 | Columbus | A61B 5/150641 422/537 |
| 5,324,256 A | * | 6/1994 | Lynn | A61B 5/150992 600/577 |
| 5,487,733 A | * | 1/1996 | Caizza | A61M 5/3275 604/110 |
| 5,591,334 A | * | 1/1997 | Shimizu | F24F 6/16 210/243 |
| 6,537,257 B1 | | 3/2003 | Wien | |
| 7,056,306 B1 | | 6/2006 | Halseth et al. | |
| 7,238,172 B2 | * | 7/2007 | Bertheas | A61M 5/158 604/177 |
| 7,594,895 B2 | | 9/2009 | Diermann et al. | |
| 7,608,042 B2 | | 10/2009 | Goldberger et al. | |
| 7,846,132 B2 | * | 12/2010 | Gravesen | A61M 5/158 604/93.01 |
| 2002/0077564 A1 | * | 6/2002 | Campbell | A61B 8/4461 600/549 |
| 2007/0260213 A1 | * | 11/2007 | Williams | A61M 5/172 711/100 |
| 2009/0095679 A1 | * | 4/2009 | Demers | A61M 1/1613 210/101 |
| 2009/0216174 A1 | | 8/2009 | Nardeo | |
| 2012/0016266 A1 | * | 1/2012 | Burkholz | A61B 5/150992 600/581 |
| 2013/0211330 A1 | | 8/2013 | Pederson et al. | |
| 2014/0188002 A1 | | 7/2014 | Close et al. | |
| 2015/0080857 A1 | * | 3/2015 | Stroup | A61M 39/04 604/110 |
| 2017/0056639 A1 | * | 3/2017 | Ma | A61M 25/002 |

FOREIGN PATENT DOCUMENTS

| | | |
|---|---|---|
| WO | WO 97/45714 | 12/1997 |
| WO | WO 2006/039310 | 4/2006 |

\* cited by examiner

APPARATUS AND METHOD FOR TAKING A SAMPLE FROM A FLUID-CONDUCTING SYSTEM

The present invention relates to an apparatus and to a method for taking a sample from a fluid-conducting system. The present invention furthermore relates to a blood treatment device.

It is known from the prior art to take samples from fluid-conducting systems such as extracorporeal circuits of blood treatment devices, e.g. manually by means of a syringe. For this purpose, a sample taking point, which is designed, for example as a septum, a luer connector, a T piece or a 3-way valve is provided at the hose system.

An advantage of a septum over the other named sample taking apparatus comprises the fact that it can be integrated in the fluid-conducting system with a favorable flow and also has advantages over the other named apparatus during the actual sample taking. A sealed access to the fluid or to the interior of the fluid-conducting system which is of a fail-safe manner can thus be established by means of a cannula. Also, no liquid escapes after the removal of the cannula since the septum closes automatically. The septum thus has a connection function and a valve function.

In clinical practice, the sample taking takes place by hand by means of a syringe through the septum. This brings about the disadvantage that the person being treated is exposed to a certain risk of injury associated with a risk of infection.

A syringe is known from U.S. Pat. No. 6,537,257 B1 whose tip is surrounded by a sleeve when not in use, the sleeve having a septum which is pierced when the syringe is used. US 2009/0216174 A1 discloses a multi-lumen catheter, wherein a lumen of the catheter can be closed by a cover flap for the purpose of flushing.

US 2013/0211330 A1 discloses an apparatus for injection having a cartridge movably received in a housing and having a needle covered by a septum in the unused state. The cartridge is moved toward the needle for the injection, with the needle penetrating the septum.

U.S. Pat. No. 7,594,895 B2 discloses a multi-lumen perfusion apparatus. An apparatus for the automated taking of a blood sample is known from U.S. Pat. No. 7,608,042 B2 which serves the monitoring of the blood composition of a patient. The blood is taken and analyzed and the measured parameter value is displayed.

It is the underlying object of the present invention to further develop an apparatus of the initially named kind such that the risk of injury on the sample taking is reduced with respect to the known procedure.

This object is achieved by an apparatus having the features of characterization 1.

Provision is accordingly made that the apparatus has at least one adapter which has at least one septum and at least one cannula which can be displaced relative to the septum, wherein the cannula can be displaced such that it penetrates the septum in a sample taking position and does not penetrate the septum in a flushing position, and wherein the adapter has at least one flushing region for a flushing medium which is arranged such that it is in fluid communication with the inner space of the cannula in the flushing position of the cannula. The apparatus furthermore has at least one receiving region having locking means for the fluid-conducting system by which the fluid-conducting system can be fixed in a defined position relative to the adapter.

It is possible by the present invention to take a sample from the fluid-conducting system which is located in the named receiving region of the apparatus without there being any risk of injury. After the insertion of the fluid-conducting system into the receiving region, the cannula is displaced manually or by means of a driven displacement mechanism such that it moves into the sample taking position, that is into the position in which its inlet is in fluid communication with the interior of the fluid-conducting system.

In a preferred embodiment of the invention, the fluid-conducting system in turn has a septum so that two septa are provided in total in this case of which one is an element of the fluid-conducting system and the other is an element of the named adapter of the apparatus.

The fluid-conducting system, and preferably its septum, has a fixed, defined position relative to the adapter and thus also relative to the cannula due to the locking means.

The term "adapter" is to be understood broadly and comprises any desired unit in which the septum and the cannula as well as the flushing region are arranged. A special adaptation to other elements of the apparatus can be provided, but is not absolutely necessary. The adapter preferably has at least one housing in which the cannula is arranged displaceably to and fro.

Provision is preferably made that the fluid-conducting system is fixable or fixed relative to the adapter by shape matching. A mechanically lockable coupling can thus be carried out, for example, directly at the septum of the apparatus or also indirectly via a console. The console can, for example, be configured as an element of a blood treatment device and can hold the adapter.

The adapter itself has a cannula displaceable relative to its housing and thus also to its septum. The displacement of the cannula allows a puncturing in this sample taking position and thus a fluid connection to the fluid-conducting system.

The cannula is arranged in the flushing position such that its interior can be flushed or contacted by a flushing medium (e.g. water, air or a calibration solution) or by a disinfecting medium.

A further, separate fluid communication with at least one further medium, namely with a flushing medium, disinfecting medium, etc. is thus possible.

The establishment of this connection takes place by the immersion or dipping of the cannula through the septum of the adapter into the flushing region and thus in a region of the adapter which is sealed with respect to the surrounding and with respect to the fluid-conducting system and which preferably has its own fluid connector for the flushing or disinfecting medium.

The receiving region can be arranged at or in the adapter itself and/or at or in a console on which the adapter is arranged. The console can be an element of a blood treatment device, preferably of a dialysis device. It is also conceivable that the receiving region is arranged between the adapter and the console.

The displacement mechanism for displacing the cannula can be manually actuable or can also be connected to a drive element such that the drive element actuates the displacement mechanism. An automated sample taking is possible in this manner.

Provision is made in a further preferred embodiment of the invention that the septum of the adapter flows through the inner lumen of the cannula, through the sample in which the sample taking position is sealingly closed with respect to the flushing region fluid.

It is preferably achieved by the locking means that the septum of the fluid-conducting system is arranged behind the septum of the adapter so that the cannula first penetrates the septum of the adapter and then the septum of the fluid-conducting system on the movement from its flushing position into the sample taking position.

The cannula end, that is the sample channel inlet, can thus open into different channel regions respectively sealed per se by the displacement of the cannula in its axial direction. This sealing preferably takes place by septa arranged behind one another.

The apparatus can furthermore be equipped with a sample taking vessel and/or a conveying device and/or a measuring device, wherein the conveying device, e.g. in the form of a vacuum pump, serves for taking the sample through the cannula in the sample taking position and the measuring device serves for measuring at least one parameter of the sample taken.

The fluid-conducting system is preferably a hose system or a section of a hose system of a blood treatment device such as a dialysis device. In a preferred embodiment, it is an extracorporeal circuit or also a dialyzate circuit (or a section thereof) of a blood treatment device and in particular of a dialysis device.

In the forwardmost position, that is in the sample taking position, a sample, that is e.g. blood or dialyzate, an be taken after the piercing of the septum of the blood hose or of the dialyzate hose. The sample channel is flushed after the intake of the blood sample or of the dialyzate sample.

For this purpose, the cannula is moved into the flushing position completely decoupled from the blood hose or dialyzate hose or from another fluid-conducting system. In this second position, the cannula tip is located in the flushing region, that is on this side of the two septa.

The flushing of the cannula exterior and/or of the cannula interior can take place, for example, by means of filtered sterile air or flushing solution, calibration solution or disinfecting solution. It can be introduced from the flushing region into the sample channel, that is into the inner lumen of the cannula.

The present invention furthermore relates to an apparatus in accordance with claim 10.

This apparatus for taking a sample from a fluid-conducting system is characterized in that it has at least one adapter and at least one receiving region in which the at least one fluid-conducting system is located, wherein the receiving region is formed with locking means for the fluid-conducting system by which the fluid-conducting system is fixed at a defined position relative to the adapter, wherein the adapter comprises at least one cannula arranged displaceably relative to the fluid-conducting system, wherein the fluid-conducting system has at least one septum, and wherein the cannula is displaceable such that it penetrates the septum of the fluid-conducting system in a sample taking position and does not penetrate this septum in a flushing position.

In this case, only one single septum is thus provided, namely that of the fluid-conducting system. The adapter is configured without a septum.

The adapter can have a flushing region for flushing the cannula, but can also be configured without a flushing region. In the latter case, the flushing of the cannula takes place by means of air. The cannula tip is not located in a first flushing region in the flushing position, but lies open.

With this apparatus, the fluid-conducting system provided with at least one septum is introduced in the receiving region and the cannula is subsequently moved such that it penetrates the septum so that the sample can be taken. The cannula is subsequently moved back into the flushing position in which the cannula tip is no longer located within the fluid-conducting system, but rather lies free or is also arranged in a flushing region.

The apparatus in accordance with characterization 10 can be configured in accordance with one of the characterizations 1 to 9. It is preferred if the apparatus in accordance with characterization 10 is configured in accordance with one of the characterizations 2 to 4, 7 or 8.

The present invention furthermore relates to a blood treatment device, in particular to a dialysis device, having at least one apparatus in accordance with one of the characterizations 1 to 11. The blood treatment device can, for example, have at least one control unit which controls the apparatus such that the cannula is introduced into the fluid-conducting system placed into the receiving region for the purpose of the sample taking.

This can preferably take place in an automated manner.

It is conceivable that the sample taking and/or the flushing procedures are carried out automatically once or a plurality of times at specific points in time or on specific incidents, for example before and/or after a blood treatment by the blood treatment device.

If a flushing procedure is carried out regularly, there is no risk of the sample channel, that is of the lumen of the cannula, being blocked by clotted blood. No intermixing of the individual sample also takes place due to the flushing free of the sample taking line.

It is a substantial advantage that there is no risk of injury for the user at the sharp cannula.

Means are preferably present which only allow a puncturing, that is a movement of the cannula into the sample taking position, when the fluid-conducting system is arranged in the receiving region. If it has a septum, provision can be made that a sample taking is only released when a septum is coupled to the sample adapter. This can be ensured both by a mechanical cam or by a mechanical element and by a sensor or a control unit.

If it is found by these means that no fluid-conducting system is located in the receiving region, it is conceivable that a movement of the cannula into the sample taking position is prevented by blocking means.

The present invention furthermore relates to a method for taking a sample from a fluid-conducting system by means of an apparatus having the features in accordance with one of the characterizations 1 to 11 or by means of a blood treatment apparatus having the features of characterization 12 or characterization 13, wherein the cannula is moved manually or by means of a drive element into the fluid-conducting system after the placement of a fluid-conducting system into the receiving region and subsequent to this a sample is taken from the fluid-conducting system.

In this respect, the fluid-conducting system can be fixed in the receiving region by a shaped-matched connection, such as by a latching, or by a clamping connection.

It is furthermore conceivable that the sample taking takes place in time or event controlled manner and at least preferably in an automated manner.

Provision is made in a further preferred embodiment that a flushing of the cannula is carried out after sample taking. The flushing procedure is preferably initiated automatically.

Provision is made in a conceivable embodiment that the blood treatment device transmits a signal to a sample taking control unit for controlling the sample taking. It polls the connected measuring device as to whether it is ready to accept a sample. If this is the case, a fluid connection is established as described in more detail above. This connection of the fluid-conducting system to the apparatus is locked. This means that the septum of the fluid-conducting system and also the adapter are fixed both with respect to one another and also in a console (where present) in a shape-matched manner. This shape-matched fixing can be achieved, for example, by one or more pins which engage into one or more grooves.

Once the sample taking is concluded, the cannula is decoupled from the fluid-conducting system and is again moved into the flushing position.

As a further embodiment, the cannula can also be hermetically sealed with respect to the flushing space in the flushing position by means of a bellows.

This has the additional advantage that no surfaces coming into contact with blood can come into contact with the atmosphere.

Further details and advantages of the invention will be explained in more detail with reference to an embodiment shown in the drawing.

Figure 2:
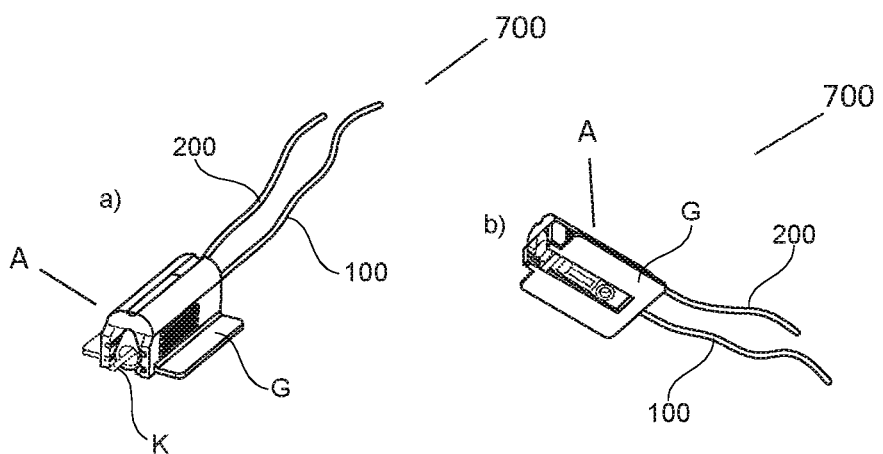
Figure 3:
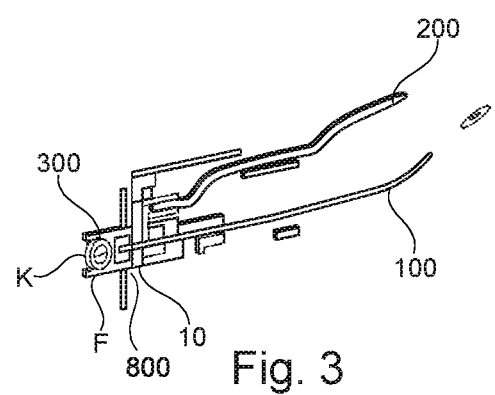
Figure 4:
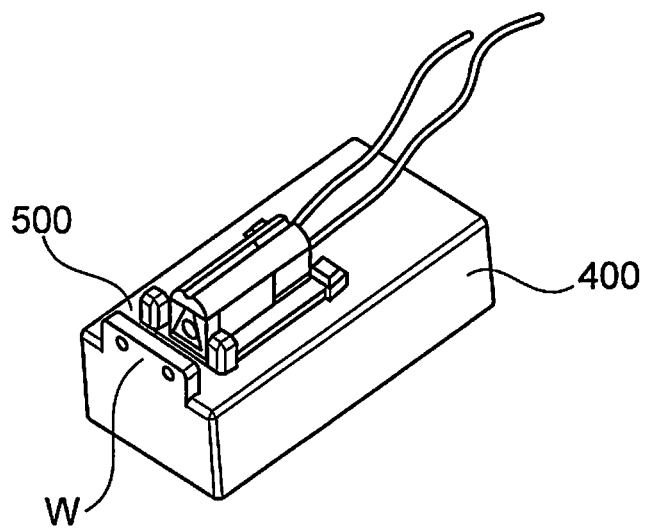

There are Shown:

FIG. 1: a schematic sectional view through the adapter in the flushing position and in the sample taking position;

FIG. 2: different perspective views of the adapter in accordance with the invention;

FIG. 3: a longitudinal section through the adapter in accordance with FIG. 2 with an inserted fluid-conducting system;

FIG. 4: a perspective view of the adapter with console; and

Figure 5:
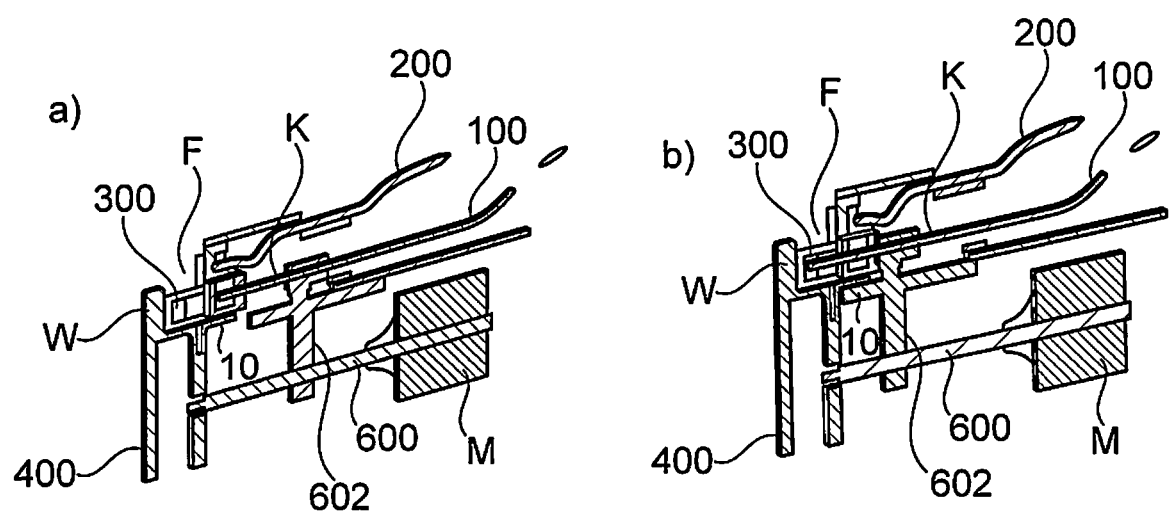

FIG. 5: sectional views through the arrangement in accordance with FIG. 4 with different positions of the cannula.

FIG. 1a) shows the septum of the apparatus in accordance with the invention by the reference numeral 10.

In the position shown in FIG. 1a), the cannula K is located in the flushing position, that is the cannula tip KS does not penetrate the septum.

The cannula has an inner lumen 20 and an outer lumen 30 which is arranged concentrically about the former.

Reference numeral 40 characterizes a connector for a flushing or disinfecting agent which enters into the flushing region 50 in the direction of the arrow. As can be seen from FIG. 1a), the flushing agent or disinfecting agent first flows through the outer lumen and then enters into the inner lumen 20 through the cannula tip KS. The flushing or disinfecting agent is discarded after the exiting from the inner lumen 20 at the point 22.

It is alternatively also possible that the reference numeral 40 not only forms the inlet for the flushing or disinfecting agent, but also forms the outlet.

If a sample is to be taken, the cannula K Is displaced to the left in accordance with FIG. 1 so that the tip KS of the cannula K pierces the septum 10, as is shown in FIG. 1b). In this position, the sample is conducted in accordance with FIG. 1b) in the direction of the arrow through the inner lumen 20, e.g. to a sample taking vessel, to a measuring device, etc. The sample taking can take place, for example, in that a vacuum is applied in the cannula 20 or in the inner lumen 20.

Reference symbol S designates a position at which the cannula K is in communication with the interior of the septum 10 such that a fluid-tight connection results. This means that there is no fluid communication between the outer lumen 30 and the inner lumen 20. This brings about the advantage that it is definitely precluded that a flushing medium moves out of the outer lumen 30 into the inner lumen 20, and thus into the fluid-conducting system, on the sample taking.

FIG. 2a) shows the apparatus of the invention 700 in a perspective view obliquely from above the adapter A with the housing G and the moved out cannula K. Reference numeral 100 designates a hose which is in fluid communication with the inner lumen 20 of the cannula and through which the sample taken is e.g. conducted to an analysis unit. Reference numeral 200 designates a hose by means of which flushing or disinfecting agent, etc. can be introduced into the flushing region 50.

FIG. 2b) shows the arrangement in accordance with FIG. 2a) in a view obliquely from below with a retracted cannula.

FIG. 3 shows in a longitudinal sectional view the adapter in accordance with the invention with a fluid-conducting system F coupled thereto via locking means 800. The fluid-conducting system F is mechanically fixed in a specific position relative to the adapter and in turn has a septum 300. On the movement of the cannula from the flushing position into the sample taking position shown in FIG. 3, the cannula tip first penetrates the septum 10 of the adapter and then the septum 300 of the fluid-conducting system F.

FIG. 4 shows the arrangement of the adapter in accordance with FIG. 2 or in accordance with FIG. 3 on a console 400. This console can, for example, be an element of a blood treatment device. As can be seen from FIG. 4, the elongate receiving region 500, which is suitable and intended for the insertion of a hose, e.g. from an extracorporeal blood circuit, is located between the end face of the adapter and a wall W of the console 400.

FIG. 5 shows a sectional representation through the arrangement in accordance with FIG. 4 with a fluid-conducting system F placed in the receiving region 500.

FIG. 5a) shows the arrangement of the fluid-conducting system between the wall W of the console 400 and the end face of the adapter. In this position, the cannula K is retracted and is located in its flushing position in which it does not penetrate either the septum 10 or the septum 300. An electric motor is designated by the reference symbol M and is connected to a spindle 600 which is set into a rotary motion in operation of the motor. The rider 602, which is in turn connected to the cannula K, is arranged movably to and fro on this spindle. The cannula K can thus be moved to the left or to the right in accordance with FIG. 5, that is into the sample taking position or into the flushing position, by the actuation of the motor.

FIG. 5a) shows the cannula K in the flushing position and FIG. 5b) in the sample taking position.

It is possible by the present invention to take a sample, e.g. from the extracorporeal blood circuit of a blood treatment device such as a blood treatment device, without a risk of injury being present for the user due to the tip of the cannula.

An automated sample taking can furthermore take place, e.g. triggered by a control or regulation unit, not shown, which moves the cannula K into the sample taking position at specific time intervals.

A sample taking vessel, a measuring device, etc. can be connected to the hose 100 and can analyze the sample taken.

The sample taking can take place at specific points in time or also on the occurrence of specific events such as before and after a blood treatment.

The Invention is Represented in the Following Characterizations:

Characterization 1. An apparatus for sample taking from a fluid-conducting system, characterized in that the apparatus has at least one adapter which comprises at least one septum and at least one cannula displaceable relative to the septum, wherein the cannula is displaceable such that it penetrates the septum in a sample taking position and does not penetrate the septum in a flushing position; and wherein the adapter has at least one flushing region for a flushing medium which is arranged such that it is in fluid communication with the inner space of the cannula in the flushing position of the cannula; and wherein the apparatus has at least one receiving region having locking means for the at least one fluid-conducting system by which the fluid-conducting system is fixable in a defined position relative to the adapter.

Characterization 2. An apparatus in accordance with characterization 1, characterized in that the locking means fix the fluid-conducting system relative to the adapter by shape matching.

Characterization 3. An apparatus in accordance with characterization 1 or characterization 2, characterized in that the receiving region is located at or in the adapter and/or at or in a console on which the adapter is arranged; or in that the receiving region is arranged between the adapter and the console.

Characterization 4. An apparatus in accordance with one of the preceding characterizations, characterized in that at least one displacement mechanism for displacing the cannula is present which is manually actuable or which is connected to a drive element which actuates the displacement mechanism.

Characterization 5. An apparatus in accordance with one of the preceding characterizations, characterized in that the septum is arranged such that it terminates the inner space of the cannula in a fluid-tight manner with respect to the flushing region in the sample taking position.

Characterization 6. An apparatus in accordance with one of the preceding characterizations, characterized in that the fluid-conducting system is located in the receiving region, with the fluid-conducting system in turn having at least one septum which is aligned with the septum of the adapter in the displacement direction of the cannula.

Characterization 7. An apparatus in accordance with characterization 6, characterized in that the fluid-conducting system is a hose and preferably an extracorporeal blood circuit or a dialyzate circuit of a blood treatment device.

Characterization 8. An apparatus in accordance with one of the preceding characterizations, characterized in that the apparatus has means for receiving a fluid sample from the fluid-conducting system and/or has at least one sample taking vessel for receiving such a fluid sample and/or has a measuring device for measuring at least one parameter of the fluid of the fluid sample from the fluid-conducting system which are directly or indirectly in fluid communication with the inner space of the cannula.

Characterization 9. An apparatus in accordance with one of the preceding characterizations, characterized in that the flushing region is filled with sterile air, flushing solution, calibration solution or disinfecting solution; and/or in that the flushing region is in fluid communication with a connector which is in turn connected or connectable to a source for sterile air, flushing solution, calibration solution or disinfecting solution.

Characterization 10. An apparatus for sample taking from a fluid-conducting system, characterized in that the apparatus has at least one adapter and at least one receiving region in which the at least one fluid-conducting system is located, wherein the receiving region is formed with locking means for the fluid-conducting system by which the fluid-conducting system is fixed at a defined position relative to the adapter, wherein the adapter comprises at least one cannula arranged displaceably relative to the fluid-conducting system, wherein the fluid-conducting system has at least one septum, and wherein the cannula is displaceable such that it penetrates the septum of the fluid-conducting system in a sample taking position and does not penetrate this septum in a flushing position.

Characterization 11. An apparatus in accordance with characterization 10, characterized in that the apparatus is configured in accordance with the characterizing portion of one of the characterizations 2 to 4, 7 or 8.

Characterization 12. A blood treatment device, in particular a dialysis device, having at least one apparatus in accordance with one of the characterizations 1 to 11.

Characterization 13. A blood treatment device in accordance with characterization 12, characterized in that the device has at least one control unit which controls the apparatus such that the cannula is introduced into the fluid-conducting system inserted into the receiving region for the purpose of the sample taking, with provision preferably being made that the control unit is configured such that is carries out the sample taking in a time-controlled or incident-controlled manner.

Characterization 14. A method for taking a sample from a fluid-conducting system by means of an apparatus having the features in accordance with one of the characterizations 1 to 11 or by means of a blood treatment device having the features in accordance with one of the characterizations 12 or 13, characterized in that the cannula is moved manually or by means of a drive element into the fluid-conducting system after the placement of a fluid-conducting system into the receiving region and subsequent to this a sample is taken from the fluid-conducting system.

Characterization 15. A method in accordance with characterization 14, characterized in that the fluid-conducting system is fixed by a shape-matched connection in the receiving region.

Characterization 16. A method in accordance with one of the characterizations 14 or 15, characterized in that the sample taking takes place in a time or incident controlled manner.

Characterization 17. A method in accordance with one of the preceding characterizations, characterized in that a flushing of the cannula is carried out after the sample taking, with provision preferably being made that the flushing procedure is automatically initiated.

The invention claimed is:

1. An apparatus for sample taking from a fluid-conducting system, characterized in that the apparatus has
   at least one adapter which comprises
     at least one septum and at least one cannula having an inner space displaceable relative to the at least one septum, wherein the at least one cannula is displaceable such that the at least one cannula penetrates the at least one septum in a sample taking position and does not penetrate the at least one septum in a flushing position, wherein the adapter has
   at least one flushing region for a flushing medium which is arranged such that the at least one flushing region is in fluid communication with the inner space of the at least one cannula in the flushing position of the at least one cannula,
   locking means for the fluid-conducting system by which the fluid-conducting system is fixable in a defined position relative to the adapter,
   a displacement mechanism for displacing the at least one cannula and comprising an electric motor connected to a spindle connected to a rider connected to the at least one cannula, wherein the spindle is set into rotary motion by actuating the motor and wherein the rider is arranged movably to and fro on the spindle, such that at least one cannula is moved into the sample taking position or into the flushing position by actuating the motor, and a vacuum pump for taking the sample through the at least one cannula in the sample taking position.

2. An apparatus in accordance with claim 1, characterized in that the locking means fix the fluid-conducting system relative to the adapter by shape matching.

3. An apparatus in accordance with claim 1, characterized in that the locking means is located at or in the adapter and/or at or in a console on which the adapter is arranged; or in that the locking means is arranged between the adapter and the console.

4. An apparatus in accordance with claim 1, characterized in that the at least one septum is arranged such that the at least one septum terminates the inner space of the at least one cannula in a fluid-tight manner with respect to the flushing region in the sample taking position.

5. An apparatus in accordance with claim 1, characterized in that the fluid-conducting system has at least one septum which is aligned with the at least one septum of the adapter in the displacement direction of the at least one cannula.

6. An apparatus in accordance with claim 5, characterized in that the fluid-conducting system is a hose and an extracorporeal blood circuit or a dialyzate circuit of a blood treatment device having at least one control unit controlling the apparatus such that the at least one cannula is introduced into the fluid-conducting system for the purpose of the sample taking, wherein the control unit is configured to carry out the sample taking in an incident-controlled manner.

7. An apparatus in accordance with claim 1, characterized in that the apparatus has means for receiving a fluid sample from the fluid-conducting system and/or has at least one sample taking vessel for receiving such a fluid sample and/or has a measuring device for measuring at least one parameter of the fluid of the fluid sample from the fluid-conducting system which are directly or indirectly in fluid communication with the inner space of the at least one cannula.

8. An apparatus in accordance with claim 1, characterized in that the flushing region is filled with sterile air, flushing solution, calibration solution or disinfecting solution; and/or in that the flushing region is in fluid communication with a connector which is in turn connected or connectable to a source for sterile air, flushing solution, calibration solution or disinfecting solution.

9. A blood treatment device, characterized in that the blood treatment device is a dialysis device, having at least one apparatus in accordance with claim 1.

10. A blood treatment device in accordance with claim 9, characterized in that the device has at least one control unit which controls the apparatus such that the at least one cannula is introduced into the fluid-conducting system for the purpose of the sample taking, with provision being made that the control unit is configured such that is carries out the sample taking in a time-controlled or incident-controlled manner.

11. A method for taking a sample from a fluid-conducting system by means of an apparatus having the features in accordance with claim 1, characterized in that the at least one cannula is moved by the drive element into the fluid-conducting system and subsequent to this a sample is taken from the fluid-conducting system.

12. A method in accordance with claim 11, characterized in that the fluid-conducting system is fixed by a shape-matched connection with the adapter.

13. A method in accordance with claim 11, characterized in that the sample taking takes place in a time or incident controlled manner.

14. A method in accordance with claim 11, characterized in that a flushing of the at least one cannula is carried out after the sample taking, with provision being made that the flushing procedure is automatically initiated.

15. An apparatus for sample taking from a fluid-conducting system, characterized in that the apparatus has at least one adapter with locking means by which the fluid-conducting system is fixed at a defined position relative to the adapter, wherein the adapter comprises at least one cannula arranged displaceably relative to the fluid-conducting system, wherein the fluid-conducting system has at least one septum, and wherein the at least one cannula is displaceable such that the at least one cannula penetrates the at least one septum of the fluid-conducting system in a sample taking position and does not penetrate the at least one septum in a flushing position, and a displacement mechanism for displacing the at least one cannula and comprising an electric motor, such that at least one cannula is moved into the sample taking position or into the flushing position by actuating the motor, and a vacuum pump for taking the sample through the at least one cannula in the sample taking position.

16. An apparatus in accordance with claim 15, characterized in that the locking means fix the fluid-conducting system relative to the adapter by shape matching.

17. A method for taking a sample from a fluid-conducting system by means of a blood treatment device, characterized in that the blood treatment device is a dialysis device, having at least one apparatus is accordance with claim 1, characterized in that the at least one cannula is moved by the drive element into the fluid-conducting system and subsequent to this a sample is taken from the fluid-conducting system.

* * * * *